United States Patent [19]

Stockel et al.

[11] Patent Number: 4,499,077

[45] Date of Patent: Feb. 12, 1985

[54] ANTI-MICROBIAL COMPOSITIONS AND ASSOCIATED METHODS FOR PREPARING THE SAME AND FOR THE DISINFECTING OF VARIOUS OBJECTS

[76] Inventors: Richard F. Stockel, 475 Rolling Hills Rd., Bridgewater, N.J. 08807; Murray Jelling, 21 Spring Hill Rd., Roslyn Heights, N.Y. 11577

[21] Appl. No.: 471,011

[22] Filed: Mar. 1, 1983

Related U.S. Application Data

[63] Continuation of Ser. No. 231,257, Feb. 3, 1981, abandoned.

[51] Int. Cl.$^3$ .................... A61K 33/20; A61K 31/14; A01N 33/12; A01N 59/00
[52] U.S. Cl. .................................. 424/149; 424/130; 514/635; 514/642
[58] Field of Search ................ 424/130, 149, 329, 326

[56] References Cited

U.S. PATENT DOCUMENTS

| | | | |
|---|---|---|---|
| 2,917,428 | 12/1959 | Hitzman | 424/130 |
| 3,123,521 | 3/1964 | Wentworth et al. | 424/130 |
| 3,689,673 | 9/1972 | Phares | 424/326 |
| 4,026,945 | 5/1977 | Green et al. | 424/78 |
| 4,029,817 | 6/1977 | Blanco et al. | 424/80 |
| 4,073,888 | 2/1978 | Snyder | 424/149 |

Primary Examiner—Douglas W. Robinson
Attorney, Agent, or Firm—Posnack, Roberts, Cohen & Spiecens

[57] ABSTRACT

An anti-microbial composition is provided comprising an aqueous solution of an oxyhalogen compound and a polymeric germicide. The oxyhalogen compound is preferably stabilized chlorine dioxide and the polymeric germicide is preferably a quaternary ammonium compound such as a copolymer of at least one difunctional tertiary amine and a dihalo organic compound such as 1,4-dihalo-2-butene, a copolymer of at least one difunctional tertiary amine, at least one monofunctional tertiary amine and a dihalo organic compound such as 1,4-dihalo-2-butene, or a polyguanide such as hydrochloride salt of poly(hexamethylene biguanide). The anti-microbial composition thus formed is used for the treatment of soft contact lenses to disinfect the same with an optimum effect while minimizing the irritant possibilities thereof and also minimizing absorption of the composition into the porous and hydrophilic surfaces of soft contact lenses such that there is a minimal release of absorbed substances after treatment.

5 Claims, No Drawings

ANTI-MICROBIAL COMPOSITIONS AND ASSOCIATED METHODS FOR PREPARING THE SAME AND FOR THE DISINFECTING OF VARIOUS OBJECTS

OTHER APPLICATIONS

This application is a continuation of my earlier application Ser. No. 231,257 filed Feb. 3, 1981, now abandoned.

FIELD OF THE INVENTION

This invention relates to anti-microbial compositions and to associated methods for preparing the same. The invention also relates to methods for disinfecting various objects and more particularly to the treatment of contact lenses such as, for example, soft contact lenses.

BACKGROUND AND PRIOR ART

Various methods are known for use in sanitization and sterilization in hospitals, operating rooms and the like as well as for other uses such as the treatment of contact lenses.

It is also known, for example, that an oxidizing agent such as chlorine dioxide or hydrogen peroxide can be used, either alone or in combination with other materials, especially those which function as stabilizers for the oxidizing agent when it is in solution.

For example, U.S. Pat. No. 3,082,146 describes the use of stabilized chlorine dioxide for treatment of water and solutions of the same are well known for their excellent bactericidal, fungicidal, and taste and odor control properties. Chlorine dioxide is known for inhibition of slime and algae in the dairy and meat industries, for treatment of industrial wastes and effluents, and for treatment in paper mills, swimming pools, animal pools and the like. Its non-toxicity and ready disappearance with no noxious by-products is a great advantage. Prior to this invention, however, stabilized chlorine dioxide has been incompatible with the eye.

As described in U.S. Pat. No. 4,029,817, hydrophilic plastic materials are used in making soft contact lenses. U.S. Pat. No. 3,503,393 to Seiderman and U.S. Pat. No. 2,976,576 to Wichterle describe processes for producing hydrophilic polymers of polyhydroxyethylmethacrylate in aqueous reaction media having a sparingly cross-linked polymeric hydrogel structure and being elastic, soft, transparent hydrogels. Other soft contact lenses are made of silicone and other suitable materials.

Hydrophilic lenses are particularly useful in opthalmology due to their ability to absorb water and swell to a soft mass of good mechanical strength, and due to their transparency with the ability to retain shape and dimensions when equilibrated in ocular fluid and in storage fluids when removed from the eye.

One problem with soft contact lenses, however, is their sterilization and cleaning. The property of hydrophilic soft lenses which allows them to absorb large amounts of water also allows preservatives which might otherwise be used for cleaning and sterilization to be absorbed and later released onto the eye. The release, furtheremore, may be much slower than the intake, thereby allowing preservatives to build up in the lenses. This can have the harmful result of damaging or staining contact lenses or harming the sensitive tissues of the conjunctivae or cornea. The problems are thoroughly discussed in the articles by J. Z. Krezanoski and R. E. Phares in the *Journal of the American Optometric Association*, Vol 43, No. 3, Pages 305–313, March, 1972. Furthermore, users of soft contact lenses are warned not to use solutions designed for hard contact lenses, for the reason that the preservatives in such solutions will be absorbed and even concentrated by the soft lens and may seriously damage the soft lenses and/or the eyes of the user upon subsequent transfer from the lenses to the ocular tissue.

As stated by R. E. Phares in U.S. Pat. No. 3,689,673, sterilization of hydrophilic soft contact lenses may be carried out by soaking in an aqueous solution containing approximately 0.001–0.01% chlorhexidine for a time sufficient to sterilize the lens.

Various related methods are disclosed in other U.S. patents. U.S. Pat. No. 3,591,329 discloses the use of a cationic resin exchange material impregnated with active metallic silver. U.S. Pat. No. 3,755,561 teaches using an aqueous solution of polyvinyl pyrrolidone, a polyalkylene glycol and thimerosal. U.S. Pat. No. 3,873,696 discloses using a combination of potassium peroxymonosulfate in the presence of sodium chloride. In U.S. Pat. No. 3,876,768 is described the use of a chlorinated trisodium phosphate material which is similar to hypochlorite. U.S. Pat. No. 3,888,782 relates to the using of chlorhexidine and polyvinyl pyrrolidone. The use of an iodoform solution containing iodine, polyvinyl alcohol and boric acid is disclosed in U.S. Pat. No. 3,911,107. U.S. Pat. No. 3,912,450 proposes using a combination of an alcoholic glutaraldehyde solution containing a surfactant in conjunction with an ultrasonic radiation device.

U.S. Pat. No. 3,888,782 more particularly discloses an aqueous, substantially isotonic cleaning and sterilizing solution for plastic hydrophilic soft contact lenses containing, as active ingredients, chlorhexidine and polyvinylpyrrolidone. The solution is said to be non-toxic to the eye of the wearer of soft contact lenses and in the presence of a suitable amount of water soluble polyhydroxyethylmethacrylate to prevent the build-up of opaque deposits on the surfaces of soft contact lenses.

U.S. Pat. No. 4,029,817 discloses that soft contact lenses may be sterilized by contacting soft lenses with a sterile, aqueous, substantially isotonic solution containing as an active ingredient, an effective amount of a quaternary ammonium compound having the structural formula

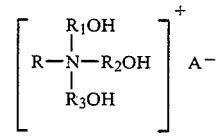

wherein R represents saturated or unsaturated alkyl residues of fatty acids and mixtures thereof containing from about 12–18 carbon atoms and preferably tallow, A is a non-toxic anion and $R_1$, $R_2$, and $R_3$ are the same or different and represent alkyl radicals having 1–3 carbon atoms; and together with a detoxifying amount of a non-toxic compound selected from the group consisting of water soluble polyhydroxyethyl methacrylate, carboxymethylcellulose, polyoxyethylene sorbitan fatty acids esters, polyoxyethylene alcohols, polyvinylpyrrolidone and mixtures thereof.

Many known quaternary ammonium compounds are generally good bactericides but are also irritating such as, for example, when they come into contact with the eye. Some of these compounds are moreover cationic and can be absorbed by porous surfaces and are difficult to remove. Where these compounds have been made less absorbent, they have never achieved the degree of perfection which would enable their use in critical applications such as with soft contact lenses.

Stabilized chlorine dioxide is known to be a powerful broad spectrum anti-microbial agent, effective in killing gram-positive and gram-negative bacteria, viruses, fungi, etc. The true composition of stabilized chlorine dioxide is an addition compound with the approximate formula of $2Na_2CO_3.3H_2O_2.ClO_2$. Stabilized chlorine dioxide has long been known as a much more effective anti-microbial agent than chlorine or hypochlorite. It completely consumes bacteria and other micro-organisms thereby preventing the formation of resistant strains. Although stabilized chlorine dioxide is a powerful oxidizing agent, its oxidation potential is less than that of hydrogen peroxide and it does not chlorinate organic compounds. It is purported to have 2.6 times the germicidal power of chlorine, yet it is 10 times as stable in aqueous solution. Stabilized chlorine dioxide is commercially available for a variety of industrial uses. However, it has never been used as an anti-microbial agent for soft contact lenses.

A 5% solution of stabilized chlorine dioxide is colorless, non-corrosive and easy to handle. It can be diluted to any concentration with water. It has government approval for many uses throughout the world. The product is inexpensive and has a long shelf life. The efficacy of stabilized chlorine dioxide increases as the pH value approaches the acid side. It does not have a characteristic chlorine-type odor. Stabilized chlorine dioxide has the unique property of oxygenation without chlorination. It destroys micro-organisms by reaction with cell structure and by speeding up the metabolism to the detriment of cell growth. It prevents immunity build-up. As it is infinitely soluble in water, any occluded chlorine dioxide that would occur within a soft lens could be readily removed by amply washing with distilled water or an isotonic solution. The oxidation potential for chlorine dioxide is $ClO_2 + 4H^+ + 5e^- = Cl^- + 2H_2O$ 1.50 volts. The oxidation potential for hydrogen peroxide is $H_2O_2 + 2H^+ + 2e^- = 2H_2O$ 1.77 volts.

Generally, U.S. Pat. No. 4,073,888 teaches the provision of a cold sterilization product for use on hard surfaces in hospitals, and kitches, for medical instruments, and so forth. At the concentrations described, it is not, however, contemplated for use in disinfecting soft contact lenses, because (1) it would be irritating to the eye and (2) absorption of the quaternary salt in soft lenses would be a major problem.

More specifically, U.S. Pat. No. 4,073,888 relates to a composition of matter which is especially adapted for hard surface, cold sanitization and sterilization especially for killing spores and, more particularly, to aqueous compositions of matter containing chlorine dioxide and certain selected quaternary ammonium salts having the formula

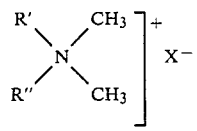

wherein R' and R" are alkyl radicals whose total carbon atoms number from 18 to 24, and preferably from 20–22. It is preferred that R' and R" be identical (symmetrical) but this is not necessary although each of the R' and R" radicals should have at least 8 carbon atoms. X is a chlorine, bromine, or any non-toxic non-interfering anion such as is known for the quaternary ammonium salts.

In order to prepare the compositions of U.S. Pat. No. 4,073,888, the chlorine dioxide may be used either in pure form as well as a stabilized chlorine dioxide complex and in solution or suspension either aqueous or non-aqueous in concentrations of from 0.1% to 6.0%. It has been found, according to U.S. Pat. No. 4,073,888, generally necessary to employ one or more emulsifiers for the disclosed compositions. Those emulsifiers are generally linear compounds which are primary alcohol ethoxylates having 12 moles of ethylene oxide and the primary alcohol portion being derived from $C_{12}$–$C_{15}$. The optimum range for use in this composition is that the primary alcohol contains from 5 to 12 moles of ethylene oxide, but from 3 to 15 moles are useful. It is believed that the sporicidal activity of these compounds is enhanced by the use of alcohol which of course is not permissible for use in the cleaning of soft contact lenses.

U.S. Pat. No. 4,026,945 discloses synthetic anti-microbial quaternary ammonium copolymers. The copolymers are prepared by the condensation of at least two difunctional tertiary amines using a molar quantity of 1,4-dihalo-2-butene equal to the molar sum of the difunctional tertiary amines in the mixture. The product is disclosed as effective for the anti-microbial treatment of water but is not good for critical applications such as soft contact lenses as mentioned above.

One of the features of the copolymers of U.S. Pat. No. 4,026,945 is that the quaternary ammonium moieties are part of the long polymeric chain rather than being quaternary ammonium moieties on branches that are bonded to the polymeric chain. Another feature is that the copolymer is a unique reaction product and not a mere mechanical mixture of separate polymers. Therefore, the copolymers cannot be separated into constituent components, as would be the case if they were mere mechanical mixtures.

Another feature of U.S. Pat. No. 4,026,945 is that the primary chemical units comprising the polymeric chain are not identically repetitive as they would be if the product were an ordinary polymer. On the contrary, the several primary chemical units of the copolymer are randomly distributed in the polymeric chain.

U.S. Pat. No. 3,428,576 describes polymeric diguanides and their salts which have been found to be effective anti-microbial agents for use with soft contact lenses. These compounds are characterized by the recurring unit

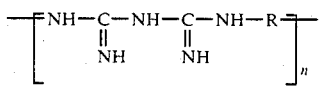

where R is a divalent radical, preferably an aliphatic hydrocarbon chain of 4 to 12 carbon atoms, and n is a number such that the molecular weight of the polydiguanide is at least about 800 and upwards to about 12,000, and higher, and preferably from about 1,000 to about 5,000. Salts of these amino/imino polymeric compounds may be made with acids such as hydrochloric acid, sulfuric acid, acetic acid, gluconic acid, etc. A preferred product is the hydrochloric acid salt of poly(hexamethylene diguanide). The product is commercially available from ICI Americas Inc. under the trade name IL-779. This product is an excellent anti-microbial agent, even in the presence of organic matter. It has a low order of toxicity and is chemically stable, non-corrosive, and odor-free. It is effective in concentrations as low as 0.001%.

In accordance with the above-described products, the required characteristics for an effective product are contained in positively-charged, nitrogen-containing cationic polymers, such as the quaternary ammonium compounds described in U.S. Pat. Nos. 4,026,945 and 4,027,020 and the amino and/or imino compounds and their salts, for example, the polydiguanides described in U.S. Pat. No. 3,428,576 as well as U.S. Pat. No. 2,643,232. These types of compounds having a plurality of cationic nitrogen species result in a more potent anti-microbial action, probably because of more points of interaction with the microbial cell wall. The other important factor is the higher molecular weight. The larger polymeric molecules are not as readily absorbed into the hydrophilic lens material, as are the small monomeric molecules.

SUMMARY OF THE INVENTION

It is an object of the invention to overcome the deficiencies of anti-microbial compositions heretofore available and specifically as noted hereinabove.

It is a further object of the invention to provide an improved anti-microbial composition and improved methods for preparing and employing the same.

It is a specific object of the invention to provide an improved anti-microbial composition particularly suitable for use with soft contact lenses and the like.

Yet another object of the invention is to provide for enhancing the effectiveness-to-concentration characteristics of oxidizing agents including oxyhalogen compounds such as, for example, stabilized chlorine dioxide.

Still another object of the invention is to enhance the effectiveness-to-concentration characteristics of polymeric germicides.

Yet another object of the invention is to provide an improved anti-microbial composition such that the absorbency of the same by porous and hydrophilic surfaces is remarkably reduced.

In achieving the above and other objects of the invention, there is provided an anti-microbial composition comprising an oxidizing agent such as an oxyhalogen compound or hydrogen peroxide, on the one hand, and a polymeric germicide, on the other. The oxyhalogen compound may be, for example, stabilized chlorine dioxide. Specifically, the polymeric germicide may be, for example, a quaternary ammonium compound or an amino and/or imino compound or salts thereof and preferably one the size and shape of which is adapted to prevent the absorption thereof by porous surfaces such as characterizies the materials from which soft contact lenses are made. These components are used in solution in water.

In one preferred embodiment of the invention, the aforesaid quaternary ammonium compound is a copolymer of at least one difunctional tertiary amine and a dihalo organic compound such as, for example, 1,4-dihalo-2-butene. Monofunctional tertiary amines are also useful. Polydiguanides are an example of amino/imino compounds which can also be used in accordance with preferred embodiments of the invention.

According to yet another aspect of the invention, there is provided a method of improving the effectiveness-to-concentration characteristics of an oxidizing agent and particularly an oxyhalogen compound such as stabilized chlorine dioxide with respect to the anti-microbial power thereof, which method comprises using the compound in the presence of a polymeric germicide such as those noted by way of example above.

According to the method of preparing an anti-microbial composition, there is comprised the combining of an oxidizing agent such as an oxyhalogen compound and the aforesaid polymeric germicide. For example, stabilized chlorine dioxide and quaternary ammonium compound by way of illustration are combined by mixing 0.001 to 0.05% by weight of the stabilized chlorine dioxide in sterilized water, and adding 0.001 to 0.05% by weight of the quaternary ammonium compound for use as a disinfectant solution for soft or hard contact lenses. For industrial uses, concentrations can range much higher and, for example, up to 5% or more depending on the specific end-use.

In still further accordance with the invention, there is provided a method of treating soft contact lenses by contacting the same with an aqueous solution of oxyhalogen compound and a polymeric germicide which are present in anti-microbial concentrations but in concentrations less than that which would irritate the human eye.

By means of the aforesaid features, there is provided a startingly enhanced effectiveness of both the oxidizing agent and polymeric germicide whereby minimum concentrations of each may be used in the anti-microbial compositions of the invention. This enables a degree of effectiveness to be achieved as is consistent with or better than results heretofore available with much smaller amounts of the components thereby assuring the avoidance of the possibility of irritation to ocular tissues or other parts of the body exposed thereto. Also obtained is the minimizing of absorbency by porous surfaces thereby preventing that such absorbed substances may be subsequently released at an undesirable time.

The above objects, features and advantages of the invention will be further illustrated and explained in the detailed description which follows hereinbelow.

DETAILED DESCRIPTION

As noted above, the invention relates to the use of oxidizing agents such as hydrogen peroxide and oxyhalogen compounds. The invention will, however, next be described hereinafter with reference to the synergistic combination of stabilized chlorine dioxide and quaternary ammonium polymeric compounds by way of illustration.

Stabilized chlorine dioxide is described in U.S. Pat. Nos. 3,082,146 and 3,123,521. It is commercially available as Anthium Dioxcide and is manufactured by International Dioxcide Inc. of New York. It has all the germicidal advantages and none of the disadvantages of chlorine dioxide gas.

At known and recommended usage dilutions, stabilized chlorine dioxide is substantially non-irritating (except in ocular situations), odorless, tasteless, non-toxic, non-mercurial, and non-explosive. Its properties are seen in the following table:

TABLE I

| Chemical and Physical Properties | |
|---|---|
| Ingredients, % | |
| Chlorine dioxide | 5.00 |
| Sodium carbonates | 3.64 |
| Inert ingredients | 91.36 |
| Concentration at 5–50° C., ppm | 50.000 |
| Specific gravity | 1.063 |
| Boiling Point, °F. | 214 |
| Freezing point, °F. | 10.5 |
| Acidity, pH | 7.2–8.5 |
| Odor | None to slight odor of ozone |
| Corrosion Concentrate | Slightly corrosive to metals |
| Recommended solutions | Noncorrosive |
| Solubility | Completely miscible in water |
| Stability | Shelf life exceeds 1 year |

The $ClO_2$ remains stable in the solution until released under control. It is believed to be the most effective known destroyer of bacteria, algae, and fungi. Stabilized $ClO_2$ has the unique property of oxygenation without chlorination. It destroys microorganisms by reaction with cell structure and by speeding up the metabolism to the detriment of cell growth. It prevents immunity build-up.

Although a given system may require feeding high concentrations (up to 15 ppm or more) of chlorine or other germicides, plus copper sulfate, it is customary to use only from 0.05 to 0.3 ppm of stabilized chlorine dioxide even where there is severe contamination by bacteria and algae.

U.S. Pat. No. 4,026,945 discloses co-polymerization products made by condensing a mixture of two or more difunctional tertiary amines and a molar quantity of 1,4-dichloro-2-butene that is equal to the molar sum of the difunctional tertiary amines in the mixture. The difunctional tertiary amines are of the type

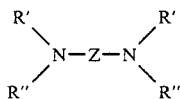

where Z consists of from one to three divalent aliphatic radicals of 2 to 10 carbon atoms which may contain 0 to 2 double bonds or 0 to 2 hydroxy substituents; wherein R' and R" are either the same or different and wherein they may be (a) primary or secondary alkyls having 1 to 20 carbon atoms, where the sum of the carbon atoms in R' and R" is no greater than 36, (b) hydroxy or dihydroxy derivatives of the aforesaid primary or secondary alkyls, (c) benzyl, (d) alkyl benzyl or (e) combined with N to form a heterocyclic group of either 5, 6, or 7 atoms.

All of the desired characteristics of the compounds of U.S. Pat. No. 4,026,945 are attained by causing a homogeneous mixture of solution of two or more difunctional tertiary amines to react with a molar quantity of 1,4-dichloro-2-butene which is equal to the molar sum of all of the components in the homogeneous mixture of solution of difunctional tertiary amines.

In this manner, if a homogeneous mixture or solution of 1,4-bis-(dimethylamino)-2-butene having the structure $(CH_3)_2-N-CH_2-CH=CH-CH_2-N-(CH_3)_2$ and N,N'-dimethyl piperazine having the structure

is reacted with a molar quantity of 1,4-dichloro-2-butene having the structure $Cl-CH_2-CH=CH-CH_2-Cl$ equal to the molar sum of the two difunctional tertiary amines, the two primary units which are part of the polymeric chain would be:

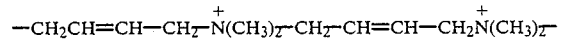

and

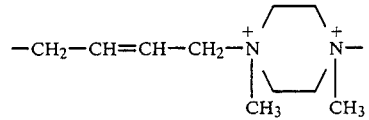

The ratio of the number of each of these units in the polymeric chain is very close to the molar ratio of the two difunctional tertiary amines in the starting mixture or solution, but the sequential order in which these two units appear in the polymeric chain is completely random, and therefore not identically repetitive.

The following examples are some of those given in U.S. Pat. No. 4,026,945.

EXAMPLE A 7.1 grams of 1,4-bis-(dimethylamino)-2-butene (0.05 mole) and 5.6 grams of diazabicyclo (2.2.2) octane (0.05 mole) are dissolved in 25 grams of water, and to the solution are added drop-wise 12.5 grams of 1,4-dichloro-2-butene (0.01 mole) at such a rate as to keep the temperature at about 60° C.–70° C. After addition is complete, and the exothermic reaction subsides, the mixture is heated in a steam bath for about 1 hour. The resulting solution contains about 50% by weight of active copolymer.

The same procedure can be repeated using as the mixtures of difunctional tertiary amines (a) 0.05 mole 1,4-bis-(morpholino)-2-butene and 0.05 mole of N,N'-dimethylpiperazine, (b) 0.05 mole of diazabicyclo (2.2.2) octane and 0.05 mole of 1,4-di-(N-homopiperidino)-2-butene, (c), 0.05 mole of 1,4-bis-(dimethylamino)-2-butene and 0.05 mole of N,N,N',N'-tetramethyl ethylenediamine. In each synthesis, the weight of water used as a solvent is approximately equal to the sum of the weights of the two difunctional tertiary amines and 1,4-dichloro-2-butene, so that the final mixture contains about 50% by weight of active copolymer.

EXAMPLE B 12.8 grams of 1,4-bis-(dimethylamino)-2-butene (0.09 moles) and 1.14 grams of N,N'-dimethyl piperazine (0.01 mole) are dissolved in 26 grams of water, and to the solution are added dropwise 12.5 grams of 1,4-dichloro-2-butene at such a rate as to keep the temperature at about 60° C.–40° C. After addition is completed, and the exothermic reaction subsides, the mixture is heated in a steam bath for about 1 hour. The resulting solution contains about 50% weight of active copolymer.

The same procedure can be repeated using as the mixtures of difunctional tertiary amines (a) 0.08 mole of 1,4-(dimethylamino)-2-butene and 0.02 mole of 1,4-bis-(N-morpholino)-2-butene, (b) 0.08 mole of 1,4-bis-(dimethylamino)-2-butene and 0.02 mole of 1,4-bis-(N-homopiperidino)-2-butene (c) 0.07 mole of 1,4-bis-(dimethylamino)-2-butene and 0.03 mole of 1,4-bis-(methyl dodecyl amino)-2-butene, and (d) 0.09 mole of 1,4-bis-(dimethylamino)-2-butene, and 0.01 mole of 1,4-bis-(methyl dodecylamino)-2-butene.

In each synthesis, the weight of the water used as a solvent is approximately equal to the sum of the weights of the two difunctional tertiary amines and 1,4-dichloro-2-butene, so that the final mixture contains about 50% by weight of active copolymer.

U.S. Pat. No. 4,027,020 discloses other useful polymeric germicides in the form of anti-microbial polymeric quaternary ammonium compounds having linear chains which terminate in quaternary ammonium moieties, such compounds being formed by polymerization which is carried out in such a manner that the linear chains thereof are terminated in random fashion, the reaction resulting in the formation of the compounds being a one-step reaction between 1,4-dihalo-2-butene and a mixture of a difunctional tertiary amine and a monofunctional tertiary amine wherein the molar quantity of the difunctional amine is greater than the molar quantity of the monofunctional amine.

The following example from U.S. Pat. No. 4,027,020 exemplifies mono- and difunctional tertiary amines:

EXAMPLE C 28.4 grams of 1,4-bis-dimethylamino-2-butene (0.2 moles) and 1.49 grams of triethanolamine (0.01 moles) were dissolved in about 55.5 grams of water in a round-bottom flask fitted with a stirrer and reflux condenser, and 25.63 grams of 1,4-dichloro-2-butene (0.205 moles) were added slowly while the mixture was stirred. The reaction mixture was heated to 60°–70° C. and maintained at that temperature, with stirring, for about 6 hours. The reaction was 98% complete, as indicated by ionic chloride analysis. The residue contained about 50%, by weight, of active material.

It has now been found that combinations of oxidizing agents such as hydrogen peroxide and oxyhalogen compounds, on the one hand, and polymeric germicides, on the other hand, permit a surprisingly large reduction in the amounts of each of these constituents which must be used. This gives a completely unexpected improvement in effectiveness-to-concentration characteristics. As a consequence, many new uses for compositions containing these two constituents are envisaged.

For example, to obtain an effective anti-microbial agent based on stabilized chlorine dioxide alone, an amount of stabilized chlorine dioxide must be employed which would be irritating in ocular applications such as the treatment of soft contact lenses. When combined with the polymeric compounds mentioned above, such relatively low concentrations of stabilized chlorine dioxide may be used that the irritant effect is avoided.

In addition, polymeric compounds have a molecular weight of at least about 800 and upwards to about 12,000, and higher, and are preferably from about 1,000 to about 5,000 and have minimal absorbency in soft contact lens material. This feature insures that the polymeric compounds are not readily absorbed and thus do not tend to concentrate on or in the soft contact lenses, or subsequently on or in the ocular tissue, thereby further assuring against irritation. This result is moreover further amplified by the fact that only a minimal amount of the polymeric compound need be used.

Other polymeric compounds which may be used in accordance with the invention are shown by supplier and patent number below.

Millmaster Onyx Corp. patents referring to polymeric quaternary ammonium compounds having germicidal properties: U.S. Pat. Nos. 3,874,870; 3,923,973; 3,928,323; 3,929,990; 3,931,319; 4,001,432; 4,005,193; 4,012,446; 4,026,945, 4,027,020; 4,036,959; 4,055,712; 4,091,113.

ICI Americas Inc. patents referring to polymeric diguanides (polydiguanides) having germicidal properties: U.S. Pat. No. 2,643,232 and 3,428,576. Polymeric diguanides are compounds containing amino/imino groups and are positively-charged, nitrogen-containing, cationic compounds. Some specific compounds which may be used include polymeric hexamethylene diguanide and are represented by the formula:*

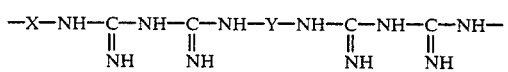

These substances can be manufactured by a process which comprises reacting a bisdicyandiamide of the formula

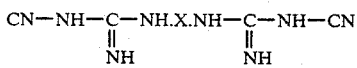

with a diamine of the formula

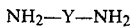

*For a definition of X and Y, see U.S. Pat. No. 2,643,232, Col. 1, lines 10–11.

In one of its simplest forms, the invention merely involves immersing soft lenses (poly(2-hydroxyethylmethacrylate, slightly cross-linked) in a solution of a combination of Onamer M and stabilized chlorine dioxide. It is desirable to make the solution isotonic and for this purpose any of the well-known agents may be used. Preferably the pH of the solution is adjusted to about 4.5–8.5 and even more preferably to about 7.4 so that the lenses will be comfortable when inserted in the eyes. Other materials commonly used in contact lens solutions may also be employed such as buffering, chelating and thickening agents.

In order to test the effectiveness of the polymeric germicide, lenses were inoculated with various test organisms and then placed in solutions of various strengths of Onamer M and stabilized chlorine dioxide.

The maximum time to reach sterility for any of the organisms was recorded. The test organisms were: Pseudomonas aeruginosa, Staphylococcus aereus, Escherichia coli, and Candida albicans.

The following results were obtained:

| | |
|---|---|
| 0.025% by wt. Onamer M (U.S. Pat. No. 4,027,020) 0.010% by wt. stabilized chlorine dioxide | 30 minutes |
| 0.009% by wt. Onamer M (U.S. Pat. No. 4,027,020) 0.008% by wt. stabilized chlorine dioxide | 1 hour |

A further example illustrates the effectiveness of combining the hydrochloride salt of poly(hexamethylenediguanide) and stabilized chlorine dioxide to reduce Aspergillus niger by 3 logs within 6 hours. IL-779 (available from ICI Americas Inc. and having a molecular weight of 1100–1300) is a twenty percent by weight aqueous solution of this salt.

| Disinfecting Solution | Microorganism | Control | 6 Hours |
|---|---|---|---|
| 0.005% polydiguanide 0.005% stabilized chlorine dioxide | A. niger | $10^8$ orgs/ml | $10^5$ orgs/ml |

All germicides are aqueous solutions and it is simply required to weight out the appropriate percentage by weight needed and dilute with sterile water. The solutions can contain 0.7% sodium chloride.

The following are exemplary concentrated formulations:

| |
|---|
| (1) Onamer M .05% by wt. Stabilized chlorine dioxide .05% by wt. Boric acid 2% by wt. Adjust to pH 7.0 Purified water Q.S. to make 100.00% by wt. |
| (2) Polydiguanide .05% by wt. Stabilized ClO$_2$ .05% by wt. Boric acid 2% by wt. Adjust to pH 7.0 Purified water Q.S. to make 100.00% by wt. |

A solution containing stabilized chlorine dioxide and polydiguanide for use in sterilizing contact lenses of all types, including hydrophilic gel lenses, may be prepared from the following formulation containing other ingredients:

| | |
|---|---|
| Stabilized chlorine dioxide | 0.005% |
| Polydiguanide | 0.005% |
| Sodium chloride | 0.50% |
| Boric acid | 0.25% |
| Trisodium Edetate | 0.05% |
| Adjust to pH 7.0 | |
| Purified water Q.S. to make | 100.00% |

Other oxidizing agents whose half cell reduction potential is at least 0.85 volts or larger can be utilized provided they meet other safety, ocular irritation and stability criteria. Preferred oxidizing agents to be used in the invention are stabilized chlorine dioxide, hypochlorite, hydrogen peroxide, and bromine chloride. The preferred range of these oxidizing agents is 0.001%–0.05% by weight in aqueous solution. The preferred range of this polymeric germicide is also 0.001%–0.05% by weight in aqueous solution.

Other auxiliary components may be included in preparing applicable formulations as for example: additional anti-microbial agents, such as chlorhexidine, organic mercurials such as thimerosal and phenylmercuric acetate; surfactants, such as sodium borate; etc.

The following additional examples demonstrate the anti-microbial effect of solutions of the present invention. All concentrations are by weight in aqueous solutions similar to the above examples.

ADDITIONAL EXAMPLE 1

Using replicate tests a solution containing 0.015% IL-779 and 0.015% stabilized chlorine dioxide, there was obtained a reduction of $\geq 99.999\%$ against Escherichia coli ATCC #11229 within a 15 minute period.

A similar result utilizing 0.02% Onamer M and 0.02% stabilized chlorine dioxide.

ADDITIONAL EXAMPLE 2

The anti-microbial effectiveness of the combination of IL-779 and stabilized chlorine dioxide was measured by a broth dilution method. The lowest concentration of this combination resulting in complete inhibition of visible growth for 48 hours represents the minimum inhibition concentration (MIC) value. These values are intended to be used as an index of efficacy for preservative applications.

| Organism | Percent by Weight | MIC ppm (in which both agents are present in equal amounts) |
|---|---|---|
| Bacteria | | |
| Escherichia coli | 0.002% | 20 |
| Pseudomonas aeruginosa | 0.008% | 80 |
| Streptococcus faecolis | 0.001% | 10 |
| Fungi | | |
| Aspergillus niger | 0.04% | 400 |
| Candida albicans | 0.03% | 300 |
| Saccharomyces turbidans | 0.003% | 30 |

This data shows that this combination has broad spectrum activity against a wide variety of test organisms.

ADDITIONAL EXAMPLE 3

Time-kill tests over replicate tests against Ps. aeruginosa and A. aerogenes with different concentrations of Onamer M-stabilized chlorine dioxide for contact periods of 30 and 60 minutes clearly demonstrates its effectiveness.

| | Equal amounts of both agents | | | |
|---|---|---|---|---|
| | | Ps. aeruginosa* # of organisms | | A. aerogenes* # of organisms |
| Conc. ppm | % by wt. | 30 min. | 60 min. | 30 min. | 60 min. |
| 5 | 0.0005% | 255 | 120 | 85 | 42 |
| 10 | 0.001% | 115 | 55 | 40 | 21 |
| 15 | 0.0015% | 61 | 26 | — | — |
| 20 | 0.002% | 25 | 15 | — | — |

*broth inoculum of $1 \times 10^6$ organisms/ml

A solution containing 0.007% of equal amounts of Onamer M and stabilized chlorine dioxide was tested on several microorganisms. Ten ml aliquots of solution were inoculated to contain approximately $10^5$ cells/ml. After six hours contact time, the remaining number of viable cells was quantitated by ten fold dilutions in broth media and plated on spread agar plates. The results are shown below:

| Microorganisms | No. of Organisms (cells) | |
|---|---|---|
| | Control | Test Formulations |
| S. aureus | $1 \times 10^5$ | $<10^2$ |
| C. albicans | $2 \times 10^5$ | $<10^2$ |
| A. niger | $1 \times 10^5$ | $<10^2$ |
| S. marcescens | $9 \times 10^5$ | $<10^2$ |

There will now be obvious to those skilled in the art many modifications and variations of the above examples. These modifications and variations will nonetheless be within the scope of the invention if defined by or equivalent to the following claims.

What is claimed is:

1. An anti-microbial composition suitable for disinfecting lenses comprising in aqueous solution 0.001 to 0.05% by weight of an oxidizing compound which is stabilized chlorine dioxide and 0.001 to 0.05% by weight of a polymeric germicide selected from the group consisting of, (a) an anti-microbial polymeric quaternary ammonium compound made by condensing a mixture of two or more difunctional tertiary amines and a molar quantity of 1,4-dichloro-2-butene that is equal to the molar sum of the difunctional tertiary amines in the mixture, the difunctional tertiary amines being of the type

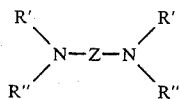

where Z consists of from one to three divalent aliphatic radicals of 2 to 10 carbon atoms which may contain 0 to 2 double bonds or 0 to 2 hydroxy substituents, wherein R' and R'' are either the same or different and wherein they be (i) primary or secondary alkyls having 1 to 20 carbon atoms, where the sum of the carbon atoms in R' and R'' is no greater than 36, (ii) hydroxy or dihydroxy derivatives of the aforesaid primary or secondary alkyls, (iii) benzyl, (iv) alkyl benzyl or (v) combined with N to form a heterocyclic group of either 5, 6, or 7 atoms, and (b) a polydiguanide which is polymeric hexamethylene diguanide.

2. An anti-microbial composition as claimed in claim 1 wherein the stabilized chlorine dioxide is an addition compound with the approximate formula of $2Na_2CO_3 \cdot 3H_2O_2 \cdot ClO_2$.

3. An anti-microbial composition as claimed in claim 1 wherein the polymeric germicide is polymeric hexamethylene diguanide.

4. A method comprising treating soft contact lenses by contacting the same with an aqueous solution of from 0.001 to 0.05% by weight of an oxidizing compound which is stabilized chlorine dioxide and from 0.001 to 0.05% by weight of a polymeric germicide selected from the group consisting of (a) an anti-microbial polymeric quaternary ammonium compound made by condensing a mixture of two or more difunctional tertiary amines and a molar quantity of 1,4-dichloro-2-butene that is equal to the molar sum of the difunctional tertiary amines in the mixture, the difunctional tertiary amines being of the type

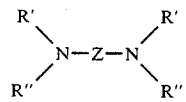

where Z consists of from one to three divalent aliphatic radicals of 2 to 10 carbon atoms which may contain 0 to 2 double bonds or 0 to 2 hydroxy substituents, wherein R' and R'' are either the same or different and wherein they may be (i) primary or secondary alkyls having 1 to 20 carbon atoms, where the sum of the carbon atoms in R' and R'' is no greater than 36, (iii) hydroxy or dihydroxy derivatives of the aforesaid primary or secondary alkyls, (iii) benzyl, (iv) alkyl benzyl or (v) combined with N to form a heterocyclic group of either 5, 6, or 7 atoms, and (b) a polydiguanide which is polymeric hexamethylene diguanide.

5. A method as claimed in claim 4 wherein the polymeric germicide is polymeric hexamethylene diguanide.

* * * * *